United States Patent
Schmitt et al.

(10) Patent No.: US 7,002,035 B2
(45) Date of Patent: Feb. 21, 2006

(54) COLOR STABILIZATION OF BASE-STABILIZED ETHYLENICALLY MODIFIED UNSATURATED MONOMERS

(75) Inventors: Bardo Schmitt, Mainz (DE); Joachim Knebel, Alsbach-Haehnlein (DE); Marianne Omeis, Zwingenberg (DE)

(73) Assignee: Roehm GmbH & Co.KG, Darmstadt (DE)

( * ) Notice: Subject to any disclaimer, the term of this patent is extended or adjusted under 35 U.S.C. 154(b) by 0 days.

(21) Appl. No.: 10/482,278

(22) PCT Filed: May 16, 2002

(86) PCT No.: PCT/EP02/05376

§ 371 (c)(1),
(2), (4) Date: Dec. 29, 2003

(87) PCT Pub. No.: WO03/006417

PCT Pub. Date: Jan. 23, 2003

(65) Prior Publication Data

US 2004/0186311 A1    Sep. 23, 2004

(30) Foreign Application Priority Data

Jun. 29, 2001  (DE) ............................... 101 31 479

(51) Int. Cl.
*C07C 69/00* (2006.01)
*C07C 69/52* (2006.01)
*C07C 69/66* (2006.01)

(52) U.S. Cl. ........................... 560/4; 560/185; 560/224
(58) Field of Classification Search .................... 560/4, 560/185, 224

See application file for complete search history.

(56) References Cited

U.S. PATENT DOCUMENTS 4,163,113 A * 7/1979 Knopf et al. ................ 560/185
5,159,106 A * 10/1992 Ritter et al. ................. 560/224
5,859,280 A * 1/1999 Arhancet ..................... 558/462

FOREIGN PATENT DOCUMENTS

| EP | 376 090 | 7/1990 |
| WO | 90/07483 | 7/1990 |
| WO | 99/01410 | 1/1999 |

* cited by examiner

*Primary Examiner*—Cecilia J. Tsang
*Assistant Examiner*—Taylor Victor Oh
(74) *Attorney, Agent, or Firm*—Oblon, Spivak, McClelland, Maier & Neustadt, P.C.

(57) ABSTRACT

The invention relates to the use of at least one compound from the tocopherol group for the color stabilization of ethylenically unsaturated monomers, particularly hydroxyalkyl(meth)acrylates, which already comprise at least one polymerization inhibitor for base stabilization or storage stabilization. Such color-stabilized and polymerization-inhibited monomers are preferably used in clearcoat and high solid paints.

17 Claims, No Drawings

COLOR STABILIZATION OF BASE-STABILIZED ETHYLENICALLY MODIFIED UNSATURATED MONOMERS

Color stabilization of base-level-stabilized ethylenically unsaturated monomers, in particular of base-level-stabilized hydroxyalkyl (meth)acrylates.

The invention is situated within the field of the stabilization of polymerizable compounds, referred to as monomers. The invention relates in particular to the color stabilization of ethylenically unsaturated monomers, in particular of hydroxyalkyl (meth)acrylates, which already have at least one polymerization inhibitor for base-level stabilization or storage stabilization.

Ethylenically unsaturated monomers tend more or less toward spontaneous polymerization. The polymerization reaction is a chain reaction which in general is triggered by free radicals. The formation of these radicals can be promoted by light and/or the effect of temperature. In order to prevent spontaneous polymerization, monomers are stabilized both during their preparation and during storage by addition of polymerization inhibitors. The number of polymerization inhibitors for the base-level or storage stabilization of ethylenically unsaturated monomers is legion.

The unwanted spontaneous polymerization of ethylenically unsaturated monomers is manifested for example in an increase in the viscosity of the monomer, which is frequently liquid under standard conditions of pressure and temperature (atmospheric pressure and ambient temperature). Whether a liquid monomer contains polymeric fractions or whether this fraction of polymeric constituents changes, i.e., usually increases, over the course of a storage period, is something which can be determined with great exactitude by means for example of nephelometric measurements.

For many applications, however, it is not only a spontaneous premature polymerization of the monomers that is problematic: the color of the monomers as well is of interest. Coating materials frequently include free-radically curing (polymerizable) monomers. In the case of clearcoat materials and high-solids coating materials particular importance is placed on their being free from intrinsic color, i.e., exhibiting no discolorations. As a consequence, neither must discolorations be carried over into the coating compositions by way of monomers which already have a tinge of color, nor must additional discolorations or tinges of color develop during the storage of the coating composition prior to its actual application. The result of both is that the clearcoat and high-solids coating materials are unusable.

Particularly in the case of hydroxyalkyl (meth)acrylates it is possible during storage, before the coating material is blended, to observe a yellow coloration which is prohibitive for the use of the monomer in such applications, for which colorlessness (absence of intrinsic color) is a prerequisite.

There accordingly exists a particular need for storage-stable (nonpolymerizing) and at the same time color-stable (nondiscoloring) ethylenically unsaturated monomers, especially hydroxyalkyl (meth)acrylates, for manifold applications, particularly as free-radically curing constituents in coating materials.

As regards the specific state of the art the following publications are cited:
WO 99/01410 (Betzdearborn Inc.)=D1;
WO 90/07483 (Henkel KGaA)=D2;
Derwent Abstract: JP 58201725 A (EISAI Co. Ltd.)=D3;
WO 99/48997 (CIBA Specialty Chemical Holding Inc.)= D4; and
DE 195 21 848 A1 (BASF AG)=D5.

D1 deals with the inhibition of the polymerization of monomers. D1 discloses in particular a method of preventing the polymerization of vinyl monomers during preparation, storage, and transit. D1 shows in particular that alpha-tocopherol is a very effective inhibitor of the polymerization of isoprene and acrylonitrile. D1 additionally describes how alpha-tocopherol and hydroquinone have a synergistic, i.e., superadditive, effect in the inhibition of the polymerization of acrylonitrile. In order to determine the effectiveness of the inhibition of polymerization, an induction time was measured in D1. This is the time up to which, under defined conditions, it was possible to suppress polymerization of the monomer by adding the inhibitors.

A further text relating to the stabilization of monomers is D2. In this document an improved process is described for preparing (meth)acrylic esters of polyhydric alcohols. In this case, stabilization with tocopherol is disclosed in the acidic esterification of methacrylic acid with alcohols. Furthermore, D2 states that, for the preparation of radiation-curable (meth)acrylic esters with high purity and in particular a low intrinsic color, three types of stabilizers are accorded particular importance. These are hydroquinone itself, di-tert-butylhydroquinone, and sterically hindered phenol compounds of the tocopherol type, especially alpha-tocopherol. According to D2 the use of di-tert-butylhydroquinone in the preparation (transesterification) leads without problems to pale-colored storage-stable (meth)acrylic esters. The use of tocopherols as well leads with comparatively few problems to pale-colored products of the desired kind. If instances of color deterioration arise during preparation, according to D2, they can be eliminated without difficulty by aftertreatment with alumina. Information on the color stabilization of monomers during storage (i.e., after preparation) cannot be inferred from D2.

The following publications relate to the stabilization of polymers.

D3 relates to the prevention of the discoloration ("browning") of polymers. It discloses a composition for coating materials or binders which comprises a copolymer of dimethylaminomethyl methacrylate and methyl methacrylate units and also tocopherol. The "browning" of the copolymer, which is readily soluble in organic solvents and water, is prevented by the addition of tocopherol.

D4 relates to the stabilizing of polymers (organic materials), particularly polyolefins, against thermal, oxidative or light-induced degradation, with a stabilizer mixture comprising at least one monomeric or oligomeric organic biphosphite together with at least one benzofuran-2-one or alpha-tocopherol (vitamin E). It is evident, however, in the examples of D4 (Example 2a) that in the case of the addition of benzofuran-2-one compound, which is understood as an alternative to tocopherol with equivalent activity, an increase in the yellowness index is observed, which in turn is an indicator that there is serious discoloration of the stabilized polymer material. An improvement in the color stabilization during extrusion can clearly be attributed here to the organic phosphite compound (Example 2b).

A further prior art document which concerns itself with the stabilization of polymeric material is D5. In this publication the stabilization of polymers of styrene or of polymers of a (meth)acrylic compound against degradation by light and/or heat and/or atmospheric oxygen, using a mixture of an organic phosphite and alpha-tocopherol is described. Concerning the color stability of the stabilized molding compound during storage, however, nothing is said.

In the light of the state indicated and discussed herein it was an object of the invention to find a possibility for effective stabilization of the color of ethylenically unsaturated monomers, especially hydroxyalkyl (meth)acrylates, which already have a base-level stabilization. A particular intention was to prevent the occurrence of discolorations during storage, which have been found in practice again and again in ethylenically unsaturated monomers stabilized adequately per se against polymerization.

These objects and also further objects which, although not stated explicitly, can nevertheless be readily inferred from the introductory discussion of the state of the art or derived therefrom as self-evident are achieved by means of a use with all of the features of the independent main claim.

Advantageous embodiments of the use according to the invention are subject matter of the claims which relate back to the independent use claim.

As a result of using at least one compound from the group of the tocopherols for the color stabilization of ethylenically unsaturated monomers, in particular of hydroxyalkyl (meth) acrylates, which already have at least one polymerization inhibitor for the purpose of base-level stabilization or storage stabilization, it is possible in a not readily foreseeable way to prevent the discoloration of monomers during storage.

Surprisingly it has been found that the addition of tocopherol to a conventionally stabilized monomer solution raises the color stability in the case of vinyl monomers, i.e., its addition in the ppm range counters the discoloration of monomers. With a series of experiments it was possible to show that the color number with a given stabilizer mixture increases continuously without tocopherol, whereas with tocopherol no increase in color, or only a moderate increase in color, was observed.

In the context of the invention a tocopherol compound is used to stabilize the color of ethylenically unsaturated monomers.

The tocopherol compounds which can be used for the purposes of the invention are chroman-6-ols (3,4-dihydro-2H-1-benzopyran-6-ols) substituted in position 2 by a 4,8,12-trimethyltridecyl radical. The tocopherols which can be used with preference in accordance with the invention include alpha-tocopherol, beta-tocopheral, gamma-tocopherol, delta-tocopherol, zeta2-tocopherol, and eta-tocopherol, all of the aforementioned compounds in each case in the (2R,4'R,8'R) form, and alpha-tocopherol in the (all-rac) form. Preference is given to alpha-tocopherol in the (2R, 4'R,8'R) form (trivial name: RRR-alpha-tocopheral) and to the synthetic racemic alpha-tocopherol (all-rac-alpha-tocopherol). Of these the last-mentioned one in turn is of particular interest in view of the relatively low price.

The amount of tocopherol compound which can be employed to stabilize the color of base-level-stabilized monomers can differ over a wide range depending on monomer and desired efficiency. For many fields of use amounts of up to 1000 ppm, based on the sum of the weights of monomer and tocopherol compound are sufficient. In many cases even very small added amounts of 10 ppm are enough to obtain a perceptible improvement in the color stability. Should less than 10 ppm be used, however, a substantial color stabilization is generally imperceptible. A favorable range for the amount to be added is therefore between 10 and 1000 ppm of tocopherol compound based on the sum of the weights of monomer and tocopherol compound. Very good results are achieved in the addition range from 100 to 800 ppm. One particular embodiment of the invention provides for use in an amount of from 200 to 600 ppm. It is especially appropriate to use about 400 ppm of tocopherol compound.

In connection with the invention ethylenically unsaturated monomers are compounds which contain at least one free-radically polymerizable double bond. These ethylenically unsaturated monomers include vinyl esters, (meth)acrylic acid, esters of (meth)acrylic acid, for example, methyl and ethyl (meth)acrylate, vinyl chloride, vinylidene chloride, vinyl acetate, styrene, substituted styrenes having an alkyl substituent in the side chain, such as α-methylstyrene and α-ethylstyrene, substituted styrenes having an alkyl substituent on the ring, such as vinyltoluene and p-methylstyrene, halogenated styrenes, such as monochlorostyrene, dichlorostyrenes, tribromostyrenes, and tetrabromostyrenes, vinyl and isopropenyl ethers, maleic acid derivatives, such as maleic anhydride, methylmaleic anhydride, maleimide, and methylmaleimide, and dienes, such as divinylbenzene, for example.

The (meth)acryl- notation embraces methacryl-, acryl-, and mixtures of both.

Preferred ethylenically unsaturated monomers are (meth) acrylic acid and also derivatives of (meth)acrylic acid. These compounds can be represented by way of example in accordance with formula 1

(I)

in which the radical $R^1$ is hydrogen or a methyl group, the radical $R^2$ is hydrogen, an aryl radical, which may also contain heteroatoms, such as phenyl and imidazole, for example, and also a straight-chain, branched or cyclic alkyl radical having up to 30 carbon atoms, which may be either saturated or unsaturated, and may also contain heteroatoms, such as nitrogen and/or oxygen, for example, such as methyl, ethyl, propyl, butyl, pentyl, hexyl, cyclopentyl, cyclohexyl, isobornyl, vinyl, propenyl, butynyl, 2-(N,N-dimethylamino)ethyl, 2-(N,N-dimethylamino)propyl, 2-hydroxypropyl, and 2-hydroxyethyl, for example.

These compounds include methyl (meth)acrylate, ethyl (meth)acrylate, propy (meth)acrylate, isoprpyl (meth)acrylate, n-butyl (meth)acrylate, isobornyl (meth)acrylate, hydroxyalkyl (meth)acrylates, such as 2-hydroxyethyl (meth)acrylate, 2-hydroxypropyl (meth)acrylate, 3-hydroxypropyl (meth)acrylate, and 3,4-dihydroxybutyl (meth)acrylate, and also aminoalkyl (meth)acrylates, such as dimethylaminoethyl methacrylate (DMAEMA).

The (meth)acrylamides corresponding to the (meth) acrylic esters are likewise a preferred group of ethylenically unsaturated monomers. They include for example N-dimethylaminopropylmethacrylamide (DMAPMA).

The ethylenically unsaturated monomers can be present individually or as a mixture in the composition of the invention.

One especially preferred group of compounds whose color is stabilized in accordance with the principle of the invention are the hydroxyalkyl (meth)acrylates.

Of particular interest in this context is the use for color stabilization of a compound selected from the group consisting of hydroxyethyl acrylate (HEA), hydroxyethyl methacrylate (HEMA), 2-hydroxypropyl acrylate (2-HPA), 2-hydroxypropyl methacrylate (2-HPMA), 3-hydroxypropyl acrylate (3-HPA), 3-hydroxypropyl methacrylate (3-HPMA), 2,3-dihydroxypropyl acrylate, 2,3-dihydroxypropyl methacrylate, 1,3-diacryloylglycerol, 1,3-dimethacryloylglycerol, trimethylolpropane monoacrylate, trimethylolpropane monomethacrylate, trimethylolpropane diacrylate, and trimethylolpropane dimethacrylate.

Esterification products of (meth)acrylic acid with polyhydric alcohols can also in particular be stabilized durably and effectively in terms of color through the inventive use of tocopherol.

Esterification products whose stabilization is particularly preferred include the (meth)acrylic esters of polyalcohols from the group embracing the following: ethylene glycol, propylene glycol, butane-1,4-diol, hexane-1,6-diol, neopentylglycol, diethylene glycol, triethylene glycol, dimethylolpropane, glycerol, trimethylolpropane, trimethylolhexane, trimethylolethane, hexane-1,3,5-triol, and pentaerythritol.

The monomers to be stabilized with respect to discoloration in accordance with the invention already include at least one stabilizing compound for the purpose of base-level stabilization. This compound is used to inhibit polymerization.

Polymerization inhibitors are already known. For example, 1,4-dihydroxybenzenes can be added for stabilization. It is, however, also possible to employ differently substituted dihydroxybenzenes. In general terms such inhibitors can be represented by the general formula (II)

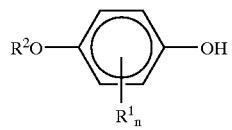

(II)

in which
$R^1$ is hydrogen, a linear or branched alkyl radical having one to eight carbon atoms, halogen or aryl, preferably an alkyl radical having one to four carbon atoms, more preferably methyl, ethyl, n-propyl, iso-propyl, n-butyl, iso-butyl, sec-butyl, tert-butyl, Cl, F or Br;
n is an integer in the range, from one to four, preferably one or two; and
$R^2$ is hydrogen, a linear or branched alkyl radical having one to eight carbon atoms or aryl, preferably an alkyl radical having one to four carbon atoms, more preferably methyl, ethyl, n-propyl, iso-propyl, n-butyl, iso-butyl, sec-butyl or tert-butyl.

It is, however, also possible to use compounds with 1,4-benzoquinone as parent compound. These can be described by the formula (III)

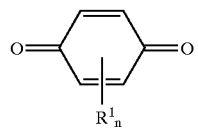

(III)

in which
$R^1$ is a linear or branched alkyl radical having one to eight carbon atoms, halogen or aryl, preferably an alkyl radical having one to four carbon atoms, more preferably methyl, ethyl, n-propyl, iso-propyl, n-butyl, iso-butyl, sec-butyl, tert-butyl, Cl, F or Br; and
n is an integer in the range from one to four, preferably one or two.

Use is also made of phenols of the general structure (IV).

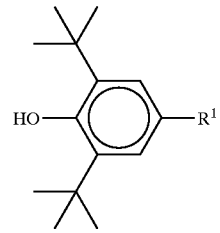

(IV)

in which
$R^1$ is a linear or branched alkyl radical having one to eight carbon atoms, aryl or aralkyl, proprionic esters with 1 to 4 valent alcohols, which may also contain heteroatoms such as S, O and N, preferably an alkyl radical having one to four carbon atoms, more preferably methyl, ethyl, n-propyl, iso-propyl, n-butyl, iso-butyl, sec-butyl, tert-butyl.

A further advantageous class of substance is represented by sterically hindered phenols based on triazine derivatives of the formula (V):

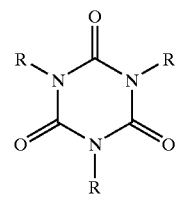

(V)

with R=compound of the formula (VI)

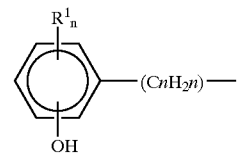

(VI)

in which
$R^1 = C_nH_{2n+1}$
with n=1 or 2.

A further group of known inhibitors are amines, especially sterically hindered amines.

These include, in particular, phenylenediamines, which can be represented by formula (VII)

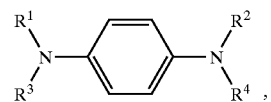

(VII)

in which $R^1$, $R^2$, $R^3$, and $R^4$ independently are hydrogen and also alkyl, aryl, alkaryl, and aralkyl radicals having in each case up to 40, preferably up to 20 carbon atoms, preferably at least one of the radicals $R^1$, $R^2$, $R^3$, $R^4$ being hydrogen.

Exemplary p-phenylenediamines include p-phenylenediamine in which the radicals $R^1$, $R^2$, $R^3$, and $R^4$ are hydrogen;

N-phenyl-N'-alkyl-p-phenylenediamines, for example, N-phenyl-N'-methyl-p-phenylenediamine, N-phenyl-N'-ethyl-p-phenylenediamine, N-phenyl-N'-propyl-p-phenylenediamine, N-phenyl-N'-isopropyl-p-phenylenediamine, N-phenyl-N'-n-butyl-p-phenylenediamines, N-phenyl-N'-isobutyl-p-phenylenediamine, N-phenyl-N'-sec-butyl-p-phenylenediamine, N-phenyl-N'-tert-butyl-p-phenylenediamine, N-phenyl-N'-n-pentyl-p-phenylenediamine, N-phenyl-N'-n-hexyl-p-phenylenediamine, N-phenyl-N'-(1-methylhexyl)-p-phenylenediamine, N-phenyl-N'-(1,3-dimethylbutyl)-p-phenylenediamine, N-phenyl-N'-(1,4-dimethylpentyl)-p-phenylenediamine;

N-phenyl-N',N'-dialkyl-p-phenylenediamines, such as N-phenyl-N',N'-dimethyl-p-phenylenediamine, N-phenyl-N',N'-diethyl-p-phenylenediamine, N-phenyl-N',N'-di-n-butyl-p-phenylenediamine, N-phenyl-N',N'-di-sec-butyl-p-phenylenediamine, N-phenyl-N'-methyl-N'-ethyl-p-phenylenediamine, for example;

N,N-dialkyl-p-phenylenediamines, such as N,N-dimethyl-p-phenylenediamine and N,N'-diethyl-p-phenylenediamine, for example;

N,N'-dialkyl-p-phenylenediamines, such as N,N'-diisopropyl-p-phenylenediamine, N,N'-diisobutyl-p-phenylenediamine, for example;

N,N'-diarylphenylenediamines, such as N,N'-diphenyl-p-phenylenediamine, for example;

N,N,N'-trialkyl-p-phenylenediamines, such as N,N,N'-trimethyl-p-phenylenediamine, N,N,N'-triethyl-p-phenylenediamine, for example.

Over and above these, phenazine dyes form a further preferred group. These include, in particular, induline and nigrosine. Nigrosine is formed by heating nitrobenzene, aniline, and hydrochloric aniline with metallic iron and $FeCl_3$. Preference is given in this context to alcohol-soluble aniline dyes, which may include, for example, 5 benzene nuclei, such as dianilido-N,N-diphenylphenosafranin. These substances are widely known and can be obtained commercially.

Particularly successful are the compounds 1,4-dihydroxybenzene, 4-methoxyphenol, 2,5-dichloro-3,6-dihydroxy-1,4-benzoquinone, 1,3,5-trimethyl-2,4,6-tris(3,5-di-tert-butyl-4-hydroxybenzyl)benzene, 2,6-di-tert-butyl-4-methylphenol, 2,4-dimethyl-6-tert-butyl-phenol, 2,2-bis[3,5-bis(1,1-dimethylethyl)-4-hydroxy-phenyl-1-oxopropoxymethyl)]1,3-propanediyl ester, 2,2'-thiodiethyl bis[3-(3,5-di-tert-butyl-4-hydroxy-phenyl)]propionate, octadecyl3-(3,5-di-tert-butyl-4-hydroxyphenyl-propionate, 3,5-bis(1,1-dimethylethyl-2,2-methylenebis(4-methyl-6-tert-butyl)phenol, tris(4-tert-butyl-3-hydroxy-2,6-dimethylbenzyl)-s-triazine-2,4,6-(1H,3H,5H)trione, tris(3,5-di-tert-butyl-4-hydroxy)-s-triazine-2,4,6-(1H,3H,5H)trione, tert-butyl-3,5-dihydroxybenzene or diphenyl-p-phenylenediamine (DPPD), of which, in turn, hydroquinone monomethyl ether (4-methoxyphenol) is especially appropriate.

The stated inhibitors are available commercially.

As base-level stabilization for ethylenically unsaturated compounds it is possible to employ the stated compounds alone or in a mixture of two or more compounds.

Based on the weight of the overall composition the fraction of the inhibitors responsible for the base-level stabilization of the monomers, individually or as a mixture, is for many applications 0.01.–0.5% (wt/wt).

For certain applications it can be of particular advantage to carry out base-level stabilization with a mixture of N,N-diethylhydroxylamine and N-nitroso-N-phenylhydroxylamine ("cupferron"). N-Nitroso-N-phenyl-hydroxylamine is an acidic compound, and its salts, such as the ammonium, aluminum, copper, lithium, sodium, potassium, and rubidium salt, for example, can likewise be used.

The combination of the compounds N,N-diethylhydroxylamine and N-nitroso-N-phenylhydroxylamine can lead to a synergistic effect in the context of the base-level stabilization.

Synergism here means that the inhibitory effect of the combination is greater than the inhibition that can be expected on the basis of the activity of the individual compounds.

In the context of use in accordance with the invention the ratio of color stabilizer to base-level stabilizer is variable. For many monomers it is appropriate to use them in a ratio (w/w) of compound from the group of the tocopherols to polymerization inhibitor (base-level stabilizer) of from 1:10 to 10:1, preferably from 1:1 to 8:1.

The inventively stabilized monomer composition may comprise further constituents. These include solvents, such as benzene, toluene, n-hexane, cyclohexane, methyl isobutyl ketone, and methyl ethyl ketone, for example.

It is additionally possible for known additives, such as antibinding agents, antistats, antioxidants, biostabilizers, chemical blowing agents, mold release agents, flame retardants, lubricants, colorants, pour improvers, fillers, glidants, adhesion promoters, catalysts, light stabilizers, optical brighteners, organophosphorus compounds, oils, pigments, impact modifiers, reinforcing agents, reinforcing fibers, weathering protectants, and plasticizers to be preferred components of the monomer composition stabilized in correspondence with the use in accordance with the invention.

The compositions stabilized by use in accordance with the invention can be obtained by mixing at least one ethylenically unsaturated monomer and an effective stabilizing amount of a base-level stabilizer and also at least one tocopherol compound.

Vinyl monomers, especially HEMA, find use in clearcoat and high-solid coating materials. The use of colorless starting materials in this context has particularly favorable consequences for the color of the end product. The use of certain hydroxyalkyl (meth)acrylates in the abovementioned applications is already described in EP 0882750 and U.S. Pat. No. 5,753,756.

The inventive and comparative examples below serve for further illustration of the present invention, without any restriction being intended thereby.

I. Methods

I.1. General Experimental Procedure

The experiments were conducted by adding additives to fully formulated monomers which in order to inhibit polymerization possessed a base-level stabilization which is indicated in the examples (stabilization with 200 ppm of hydroquinone monomethyl ether (HQME)), with the concentrations indicated in the table. The samples were subjected to a storage test in comparison to the corresponding blank samples at 50° C. In the course of this test, at certain intervals the Pt/Co color number was determined along the lines of DIN/ISO 6271 as a function of the time. In addition, nephelometry was used to determine the turbidity of the samples, so as to investigate the inhibition of polymerization.

I.2. Determination of the Turbidity of Liquid Organic Compounds (Nephelometry)

I.2.1. Principle

A light beam is passed through the sample. Photoelectric cells are used to measure the light scattered at an angle of 90°, the forward-scattered light, and the transmitted light. The ratio of the output of the photoelectric cell for the 90° measurement to the sum of the outputs of the other two photoelectric cells is formed electronically and in this way outstanding linearity is achieved and the influence of the color is excluded. As a result of the construction of the optical system the scattered light can be disregarded. Scattered light in the context of nephelometric measurements is the portion of the light which reaches the photoelement but cannot be attributed to light scattering in the sample. The samples under analysis are measured using a turbidity-measuring instrument. The HACH* Ratio turbidity meter is a laboratory nephelometer which allows turbidities of up to 199 turbidity units (NTU) to be measured on the basis of formazine even in colored samples. Solutions with a higher turbidity can also be measured following dilution of the sample, with a filtered sample solution, and on the basis of a simple calculation.

* The instrument is registered under U.S. Pat. No. 4,198,161 to the Hach Company.

I.2.2. Technical Data of the Ratio Turbidity Meter

| Calibration standard: | formazine |
| --- | --- |
| Sample size: | 30 ml |
| Cuvette: | 25 × 95 mm; glass bottles with screw cap |
| Operating temperature range: | +10° to +45° C. |
| Reaction time: | less than 15 seconds until equilibrium is reached in the greatest measuring range |
| Reproducibility: | 1% of the measuring range plus ±1 at the smallest point |
| Accuracy: | ±2% of the measuring range plus ±1 at the smallest point |
| Measuring range: | 0–200 NTU |

I.2.3. Sample Preparation a. Switch on instrument and wait for about 15 minutes for it to warm up;
b. Switch on measuring area and insert the corresponding turbidity standard and again wait for about 15 minutes;
c. The indicator must be at ±5% of the nominal value (otherwise calibration must be repeated);
d. Fill a clean cuvette up to the mark with test liquid and adjust;
e. The turbidity of the sample appears on the digital display I.2.4. Meaning and Significance of the Measurements

| <2 NTU | invisible to the eye |
| --- | --- |
| 2 to 5 NTU | just visible to the eye |
| >5 NTU | distinct turbidity |
| >20 NTU | severe turbidity |

I.3. Photometric Determination of the Platinum-cobalt Color Number of Monomers

I.3.1. Principle

The visual comparison with color standard solutions of the platinum-cobalt scale is replaced by a measurement of the absorbance of the sample at the wavelengths of 460 and 620 nm. The difference in absorbance $A_{460\ nm} - A_{620\ n} = \Delta A$ stands in a linear relation to the color unit of the platinum-cobalt standards. When the color number is plotted as a function of $\Delta A$ a calibration plot is obtained whose slope serves directly as the "factor" for the calculation of the color number. The assumption is that the sample under analysis corresponds to the color characteristic, i.e. corresponds substantially in shade to the platinum/cobalt scale. Synonyms for the platinum-cobalt color number are APHA number and Hazen number.

I.3.2. Procedure

I.3.2.1. Apparatus

Spectrophotometer or filter photometer having filters for the ranges 460 and 620 nm; 5 cm and 1 cm cuvettes Balance (d=1 mg); volumetric flask; volumetric cylinder I.3.2.2. Calibrating Substances
Potassium hexachloroplatinate (IV) ($K_2PtCl_6$)
Cobalt(II) chloride hexahydrate ($CoCl_2 \times 6H_2O$)
Conc. hydrochloric acid p.a. 32%

I.3.2.3. Establishment of the Calibration Function

I.3.2.3.1 Preparation of the Color Standard 1.245 g of hexachloroplatinate(IV) and 1.000 g of cobalt (II) chloride hexahydrate are dissolved in DI water; 118.8 ml of the conc. hydrochloric acid are added and the solution is made up to the mark with DI water in a 1000 ml volumetric flask. This solution possesses a Pt/Co color number of 500 provided that it corresponds to the limiting values indicated in the compilation below for the transmittance and absorbance when measured with the spectrophotometer in a 1 cm cuvette against DI water.

| Wavelength (nm) | Transmittance | Absorbance |
| --- | --- | --- |
| 430 | 0.759 to 0.776 | 0.110 to 0.120 |
| 455 | 0.716 to 0.741 | 0.130 to 0.145 |
| 480 | 0.759 to 0.785 | 0.105 to 0.120 |
| 510 | 0.861 to 0.881 | 0.055 to 0.065 |

I.3.2.3.2. Preparation and Measurement of the Pt/Co Standard Comparison Solutions Pt/Co standard comparison solutions for the required measurement range (0–500 of the color scale) can be prepared from the Pt/Co stock solution by introducing corresponding volumes of standard solution into 100 ml volumetric flasks which are made up to the mark with DI water. The volumes of stock solution for the desired Pt—Co standard comparative solutions can be taken from the tabular compilation below:

Pt—Co standard comparison solutions

| Color Pt—Co color number | Volume of the stock solution ml |
| --- | --- |
| 0 | 0 |
| 5 | 1 |
| 10 | 2 |
| 15 | 3 |
| 20 | 4 |
| 30 | 6 |
| 40 | 8 |
| 50 | 10 |
| 70 | 14 |
| 100 | 20 |
| 150 | 30 |
| 200 | 40 |
| 300 | 60 |
| 400 | 80 |
| 500 | 100 |

The Pt—Co standard comparison solutions prepared are measured in 5 cm cuvettes with the spectrophotometer or with a filter photometer with the corresponding filters at 460 and 620 nm. (Reference cuvette contains DI water). The Pt/Co color numbers and the associated differences in absorbance that are measured (A460 nm-A620 nm) produce a linear relationship. The slope of this calibration plot can be determined graphically or, better still, by regression calculation and serves as a basis for calculating the Pt/Co color number (=factor).

I.3.2.4. Assessing the Samples and Carrying Out Photometric Measurement

I.3.2.4.1. Visual Assessment

Prior to the actual measurement it is necessary to carry out a visual examination as to whether the sample corresponds to the color characteristic (yellow hue, for example, by comparison with the standard comparison solutions) of the Pt/Co color scale or deviates therefrom. If the latter is the case, then no measurement takes place. If the sample exhibits a turbidity, then stating the color number in accordance with the underlying color scale here makes no sense. In the case of uncolored samples, turbidities can simulate color numbers >100.

I.3.2.4.2. Photometric Measurement

If the color characteristic matches, the liquid for measurement is introduced into a 5 cm cuvette and the cuvette is sealed. It must be free from air bubbles or streaks. Then the absorbance of the sample is measured with a spectrophotometer or with a filter photometer with the corresponding filters at 460 and 620 nm against DI water and the difference in absorbance is calculated.

I.3.2.5. Calculation of the Pt/Co Color Number (APHA Number)

Pt/Co color number=$(A_{460}$ nm$-A_{620}$ nm$)\times$factor (5 cm)

Factor (varian cary 1 spectrophotometer)=755.2

Since the factor may adopt different values depending on the specific instrument, it must be determined in each case in accordance with 1.3.3.3. If absorbances <0 occur at 620 nm, then again the difference is formed; in other words, the absorbance figure at 460 nm has the numerical value of the absorbance at 620 nm added to it.

I.3.2.6. Results Reporting

If the sample is more transmittant than DI water, i.e., absorbances of between 0 and negative values are obtained at 460 and 620 nm, then fundamentally <5 is reported.

Where the calculated color number is between 0 and 5, <5 is reported.

Where the calculated color number is between 5 and 200, the result is reported rounded to whole numbers.

When the calculated color number is between 200 and 500, the result is rounded to 5 units.

I.4. Method of Determining the Polymerization Time (PT Measurement)

I.4.1. Thermal Polymerization in an Oil Bath

A test tube (18×180 mm) is filled with 20 g of the test mixture. With the aid of a specially manufactured, drilled ®Plexidur stopper a glass tube (diameter 7 mm) which has been closed by melting at one end is centered in the test tube. The length of the melt-closed glass tube is approximately 75 mm. It ends about 1.8 cm above the base of the test tube. A small amount of a high-boiling plasticizer is introduced into this glass tube, as a heat transfer medium, and an Fe/constantan thermocouple is inserted. At the beginning of the polymerization time measurement the test tube containing the test mixture is inserted into a circulation bath thermostat which has been preheated to polymerization temperature. The depth of immersion is adjusted reproducibly by means of a plastic mesh. The level of the oil bath is at least 1 cm above the level of the liquid in the test tube. Simultaneously with the insertion of the test tube into the oil bath a PC-supported temperature measuring position with six measuring points is switched on. The temperature/time plot is recorded and evaluated. After the polymerization process is substantially at an end, the measurement is terminated.

I.4.2

The measured values obtained and recorded are, in dependence on the measuring point, the time taken to achieve the temperature maximum and the peak polymerization temperature.

II. Results

II.1. HEMA—Color Study on Two Batches (A and B) Statement of the Pt—Co Color Number in Accordance with I.3.3.

The results are summarized as follows:

30° C. storage

|  | Batch A | Batch A +400 ppm tocopherol | Batch B | Batch B +400 ppm tocopherol |
| --- | --- | --- | --- | --- |
| Beginning of study | <5 | <5 | <5 | <5 |
| after 2 weeks | 10 | 8 | 7 | 8 |
| after 4 weeks | 8 | 5 | 5 | 6 |
| after 6 weeks | 13 | 10 | 10 | 10 |
| after 8 weeks | 14 | 9 | 11 | 9 |
| after 10 weeks | 15 | 9 | 13 | 9 |

50° C. storage

|  | Batch A | Batch A +400 ppm tocopherol | Batch B | Batch B +400 ppm tocopherol |
| --- | --- | --- | --- | --- |
| Beginning of study | <5 | <5 | <5 | <5 |
| after 2 weeks | 21 | 11 | 22 | 10 |
| after 4 weeks | 22 | 8 | 18 | 9 |
| after 6 weeks | 25 | 12 | 20 | 11 |
| after 8 weeks | 24 | 13 | 19 | 13 |
| after 10 weeks | 23 | 13 | 19 | 12 |

II.2. HEMA—Polymer Test on Stored Samples

Turbidity measurement in accordance with I.2., 1:9 in diethyl ether.

Statement of the NTU values.

After 10 weeks at 50° C.

|  | Additive | Turbidity |
| --- | --- | --- |
| Batch A |  | 0.35 NTU |
| Batch A | 400 ppm of tocopherol | 0.30 NTU |
| Batch B |  | 0.30 NTU |
| Batch B | 400 ppm of tocopherol | 0.29 NTU |

The turbidity values obtained unambiguously permit the conclusion that the samples contain no polymer fractions at all. Values >200 NTU were obtained on incipiently polymerized HEMA (0.05% initiator. 80° C., approx. 50 min) in the turbidity test.

The improvement in the turbidity value through the addition of tocopherol is only minimal. This means that the addition of tocopherol makes no significant contribution to the stabilization before polymerization.

In order to confirm this result a further investigation was set up.

II.3. Determination of the Polymerization Times (PT Test)

At the processing temperatures typical for the applications (e.g., in coating materials) the polymerization time of samples with base-level stabilization by HQME were investigated and were compared with the polymerization time of samples additionally containing an amount of alpha-tocopherol effective for the purpose of color stabilization.

Conditions:

Comparison sample:
Hydroxyethyl methacrylate (HEMA) stabilized with 200 ppm of hydroquinone methyl ether (HQME);

Inventive sample:
Hydroxyethyl methacrylate (HEMA) stabilized with 200 ppm of hydroquinone methyl ether (HQME) and additionally containing 400 ppm of tocopherol;
Polymerization temperature: 110° C.;
Initiator: 1.0% (w/w) tert-butyl peroctoate;

Comparison sample:
Polymerization time: 2.8 min;
Temperature maximum: 175.5° C.;
Sample in acc. with invention;
Polymerization time: 3.0 min;
Temperature maximum: 168.8° C.

These values also demonstrate that the addition of tocopherol has no significant influence on the inhibition of polymerization. In spite of this, and in a manner which was not immediately foreseeable, it is the case, however, that the color of base-level-stabilized monomers is stabilized over time.

The invention claimed is:

1. A method for color stabilization of ethylenically unsaturated monomers, comprising:
   mixing at least one tocopherol with a composition comprising one or more ethylenically unsaturated monomers and at least one polymerization inhibitor which is different from said at least one tocopherol to form a mixture, wherein the tocopherol is present in the mixture in an amount effective for color stabilization;
   wherein the tocopherol is present in an amount that leads to no increase in the Pt/Co color number measured photometrically as the absorbance between 460 and 620 nm when the mixture is stored at 50° C. for 2 to 10 weeks.

2. The method as claimed in claim 1, wherein color stabilization is measured by the Pt/Co color of a solution stored at 50° C. for from 2 to 10 weeks and the color of the mixture containing said at least one tocopherol and said polymerization inhibitor is less than the color of the composition containing said polymerization inhibitor.

3. The method as claimed in claim 1, wherein color stabilization is measured by the turbidity of a solution stored at 50° C. from 2 to 10 weeks and the turbidity of the mixture containing said at least one tocopherol and said polymerization inhibitor is less than the turbidity of the composition containing said polymerization inhibitor.

4. The method as claimed in claim 1, wherein the tocopherol is all-rac-α-tocopherol.

5. The method as claimed in claim 1, wherein the tocopherol is present in an amount of from 10 to 1,000 ppm based on the sum of the weights of the tocopherol and the ethylenically unsaturated monomer.

6. The method as claimed in claim 1, wherein the tocopherol is present in an amount of from 100 to 800 ppm based on the sum of the weights of the tocopherol and the ethylenically unsaturated monomer.

7. The method as claimed in claim 1, wherein the tocopherol is present in an amount of from 200 to 600 ppm based on the sum of the weights of the tocopherol and the ethylenically unsaturated monomer.

8. The method as claimed in claim 1, wherein the ethylenically unsaturated monomer is an hydroxy alkyl(meth)acrylate.

9. The method as claimed in claim 1, wherein the ethylenically unsaturated monomer is at least one compound selected from the group consisting of hydroxyethyl acrylate, hydroxyethyl methacrylate, 2-hydroxypropyl acrylate, 2-hydroxypropyl methacrylate, 3-hydroxypropyl acrylate, 3-hydroxypropyl methacrylate, 2,3-dihydroxypropyl acrylate, 2,3-dihydroxypropyl methacrylate, 1,3-diacryloylglycerol, 1,3-dimethacryloylglycerol, trimethylolpropane monoacrylate, trimethylolpropane monomethacrylate, trimethylolpropane diacrylate, and trimethylolpropane dimethacrylate.

10. The method as claimed in claim 1, wherein the polymerization inhibitor is a hydroquinone.

11. The method as claimed in claim 1, wherein the polymerization inhibitor is hydroquinone monomethylether.

12. The method as claimed in claim 1, wherein the tocopherol and the polymerization inhibitor are present in a ratio of from 1:10 to 10:1.

13. The method as claimed in claim 1, wherein the tocopherol and the polymerization inhibitor are present in a ratio of 1:1 to 8:1.

14. A clear coating material stabilized by the method as claimed in claim 1.

15. A composition comprising one or more hydroxy alkyl(meth)acrylates stabilized with the method as claimed in claim 1.

16. A composition comprising one or more hydroxy alkyl(meth)acrylates and one or more fillers, stabilized with the method as claimed in claim 1.

17. The method as claimed in claim 1, wherein said mixture comprises N,N-diethylhydroxylamine and N-nitroso-N-phenylhydroxylamine.

* * * * *